United States Patent [19]
Rao et al.

[11] Patent Number: 5,559,069
[45] Date of Patent: Sep. 24, 1996

[54] CATALYSTS FOR HALOGENATED HYDROCARBON PROCESSING, THEIR PRECURSORS AND THEIR PREPARATION AND USE

[75] Inventors: V. N. Mallikarjuna Rao, Wilmington; Munirpallam A. Subramanian, New Castle, both of Del.

[73] Assignee: E. I. du Pont de Nemours and Company, Wilmington, Del.

[21] Appl. No.: 249,765

[22] Filed: May 26, 1994

[51] Int. Cl.$^6$ ........................................... B01J 27/138
[52] U.S. Cl. ........................................... 502/226; 502/228
[58] Field of Search ........................................... 502/226, 228

[56] References Cited

U.S. PATENT DOCUMENTS

| | | | |
|---|---|---|---|
| 3,754,043 | 8/1973 | Bjornson et al. | 260/653 |
| 4,319,060 | 3/1982 | Cunningham et al. | 570/177 |
| 4,547,483 | 10/1985 | Muller et al. | 502/226 |
| 4,902,838 | 2/1990 | Manzer et al. | 570/151 |

FOREIGN PATENT DOCUMENTS

| | | | |
|---|---|---|---|
| 0074069 | 3/1983 | European Pat. Off. | C07C 21/24 |
| 0130532 | 1/1985 | European Pat. Off. | B01J 27/12 |
| 0548743 | 6/1993 | European Pat. Off. | C08G 65/32 |
| WO88/04108 | 6/1988 | WIPO | H01M 8/12 |
| WO92/02476 | 2/1992 | WIPO | C07C 17/24 |
| WO92/16480 | 10/1992 | WIPO | C07C 17/00 |
| WO92/16479 | 10/1992 | WIPO | C07C 17/00 |
| WO92/16482 | 10/1992 | WIPO | C07C 17/20 |

OTHER PUBLICATIONS

Gmelin's Handbuch der Anorganischen Chemie; Band 5 (Fluuor), Erster Ergänzungsband, Verlag Chemie (1926), pp. 59–73.
Chemical Abstracts: 105:8699 (1985); 92:208099 (1980); 118:136730 (1993).
Chemical Abstracts 98:40910 (1982); 88:145340 (1977).
Chemical Abstracts 71:75042 (1969); 76:118307 (1972); 79:150476 (1973).
Laligant, Y. et al, *J. of Solid State Chemistry*, 62, 274–277 (1986).
Laligant, Y. et al, *Zeitschrift fur Kristallographie*, 181, 1–10 (1987).
Laligant, Y. et al, *J. Phys. C; Solid State Phys.*, 19, 1081–1095 (1986).
Laligant, Y. et al, *J. of Solid State Chem.*, 66, 242–250, (1987).
Charpin, P. et al, *C.R. Acad. Sci. Paris*, C280, 61–64, (1975) (with abstract CA 82: 164363).
Feki, M. et al, *C.R. Acad. Sci. Paris*, 303, 441–444, (1986) (with abstract CA 106:42791).
Balcerek, T. W. et al, *J. Inorg. & Nucl. Chem.*, 40, 773–777 (1978).
Manzer, L. E. et al, *Advances in Catalysis*, 39, 329–350 (1993).
Wieghardt, K. et al, *J. of Molecular Structure*, 7, 305–313, (1971).
Demsar, A. et al, *Thermochimica Acta*, 92, 665–668, (1985).
Laligant, Y. et al, *Chemica Scripta*, 28, 101–106, (1988).

*Primary Examiner*—Asok Pal

[57] ABSTRACT

A process is disclosed for changing the fluorine content of halogenated hydrocarbons containing from 1 to 6 carbon atoms, in the presence of a multiphase catalyst, which is characterized by preparing certain single phase solid catalyst precursors containing two metal components (e.g., a divalent component of Mn, Co, Zn, Mg and/or Cd and a trivalent component of Al, Ga, Cr and/or V) which have structures that collapse at about 600° C. or less; and producing said catalyst by heating the precursor to produce a multiphase composition wherein a phase containing one of the metal components is homogeneously dispersed with a phase containing the other metal component, and at least when the precursor contains no fluoride, contacting said multiphase composition with a vaporizable fluorine-containing fluorination compound at a temperature of from about 200° C. to 450° C. Also disclosed are single phase fluoride compositions having the formula $MM'F_5(H_2O)_2$ wherein M is a divalent component selected from Mn, Co, Zn, Mg and/or Cd and M' is a trivalent component selected from Al, Ga, Cr and/or V (provided that Cr is not more than about 10 atom percent of M'); preparation of certain homogeneously dispersed multiphase catalyst compositions containing fluorides of those divalent and trivalent metal components; and certain homogeneously dispersed multiphase catalyst compositions containing fluorides of those divalent and trivalent metal components (provided that when Co is used another of said divalent elements is also used).

16 Claims, No Drawings

CATALYSTS FOR HALOGENATED HYDROCARBON PROCESSING, THEIR PRECURSORS AND THEIR PREPARATION AND USE

FIELD OF THE INVENTION

This invention relates to fluoride compositions and their preparation and use, and more particularly to fluoride catalysts, precursors for such catalysts, and preparation and use of such catalysts for processing halogenated hydrocarbons.

BACKGROUND

Numerous processes have been developed for changing the fluorine content of halogenated hydrocarbons. These include increasing the fluorine amount of halogenated hydrocarbons which are not fully fluorinated, decreasing the fluorine content of halogenated hydrocarbon containing fluorine, and redistributing the number of fluorine atoms among two or more halogenated hydrocarbon molecules which are not fully fluorinated.

Various catalysts have been proposed for use in facilitating processes such as hydrofluorination, hydrochlorination (i.e., fluorine substitution by chlorine) and disproportionation which involve halogenated hydrocarbons. See, e.g., L. E. Manzer et al., Adv. Catal. (39) pp. 329–350 (1993). The catalysts proposed include catalysts involving combinations of cations. For example, a well known class of catalysts includes metals supported on alumina or fluorinated alumina. Typically these materials are prepared by depositing a soluble salt of the metal on an alumina or aluminum fluoride support. While this method does provide a combination catalyst, the support material and the material deposited thereon are not uniformly mixed. Techniques such as coprecipitation which rely upon physical characteristics of individual components (e.g., solubility) also typically yield non-homogeneously dispersed products due to differences in physical and chemical properties of the components. There is an interest in developing means for more homogeneous dispersion of components of multiple cation catalysts which can be used for changing the fluorine content of halogenated hydrocarbons.

SUMMARY OF THE INVENTION

This invention provides a process for changing the fluorine content of halogenated hydrocarbons containing from 1 to 6 carbon atoms, in the presence of a multiphase catalyst. The process is characterized by (1) preparing a single phase solid catalyst precursor which has a structure that collapses at a temperature of about 600° C. or less and has the formula $E_u E'_{1-u} Z_v (H_2O)_w Y_z$ wherein E is at least one element selected from the group consisting of Group I through Group VIII metals of the Periodic Table, E' is at least one element other than the E elements selected from the group consisting of Group I through Group VIII metals of the Periodic Table, Z is at least one anion selected from fluoride, chloride, bromide, oxide and oxygen-containing groups which decompose at about 600° C., or less, Y is a cation which decomposes at about 600° C., or less, u is from 0.001 to 0.999, w is from 0 to about 20, z is from 0 to about 5, and v is selected to essentially balance the charge of said precursor; and (2) producing said catalyst by heating said single phase solid catalyst precursor to about 600° C. or less to produce a multiphase composition wherein a phase containing E is homogeneously dispersed with a phase containing E', and at least when said precursor contains no fluoride, contacting said multiphase composition with a vaporizable fluorine-containing fluorinating compound at a temperature of from about 200° C. to 450° C.

This invention further provides single phase fluoride compositions having the formula $MM'F_5(H_2O)_2$ wherein M is at least one divalent element selected from the group consisting of Mn, Co, Zn, Mg and Cd and M' is at least one trivalent element selected from the group consisting of Al, Ga, Cr and V, provided that Cr is not more than about 10 atom percent of M'. This invention also provides multiphase catalyst compositions consisting essentially of fluorides of at least one divalent element selected from the group consisting of Mn, Co, Zn, Mg and Cd, provided that when Co is used another of said divalent elements is also used, and at least one trivalent element selected from the group consisting of Al, Ga, Cr and V, provided that Cr is not more than about 10 atom percent of said trivalent elements, wherein phases of said divalent fluorides are homogeneously dispersed with phases of said trivalent fluorides. A homogeneously dispersed multiphase catalyst composition consisting essentially of fluorides of divalent Mn, Co, Zn, Mg and/or Cd and trivalent Al, Ga, Cr and/or V (provided that Cr is not more than about 10 atom percent of said trivalent elements) may be prepared in accordance with this invention by heating a corresponding single phase fluoride composition of the formula $MM'F_5(H_2O)_2$ or by heating a corresponding single phase fluoride composition of the formula $NH_4MM'F_6(H_2O)$, wherein M and M' are as defined above, to a temperature sufficient to substantially remove $H_2O$ (and $NH_4F$, when $NH_4^+$ is present) therein.

DETAILED DESCRIPTION

The catalytic process of this invention for changing the fluorine content of halogenated hydrocarbons containing from 1 to 6 carbon atoms employs a multiphase catalyst prepared in a manner which provides homogeneous dispersion of multiple metal components by preparing a decomposable single phase solid catalyst precursor and then converting the precursor to a multiple phase catalyst containing fluorine. A single phase catalyst precursor of the formula $E_u E'_{(1-u)} Z_v (H_2O)_w Y_z$ may be prepared by conventional synthetic techniques (e.g., crystallization). E and E' represent different metal components selected from the Group I (e.g., Cu, K and Cs), Group II (e.g., Ca, Zn, Cd and Mg), Group III (e.g., Al, Y, Ga, La and Ce), Group IV (e.g., Ti, Zr and Sn), Group V (e.g., V, Nb and Bi), Group VI (e.g., Cr, Mo and Te), Group VII (e.g., Mn and Re), and Group VIII (e.g., Pd, Pt, Co, Ru, Rh and Ir) of the Periodic Table. (The Periodic Table of the Elements as listed in the CRC Handbook of Chemistry and Physics, 64th Edition (1983) is used herein to define the elemental groups.) For example, E may be a divalent metal component such as Mn, Co, Zn, Mg and/or Cd and E' may be a trivalent metal component such as Al, Ga, Cr and/or V. Normally, the ratio of the metal components, u:(1−u), should be between 1:999 and 999:1. Z represents an anion component which includes fluoride and/or anions capable of at least partial conversion to fluoride. Suitable Z anions include fluoride, chloride, bromide, oxide and decomposable oxygen-containing groups such as nitrate, carbonate and acetate. The precursor may also contain water molecules and/or decomposable cations such as ammonium. Typically, w, the ratio of water (when present) to total metal (E+E') is about 20, or less; and z, the ratio of decomposable cations (when present) to the total metal (E+E') is about 5, or less. Preferably, w is at least 1. Generally, v, the ratio of the anion component Z to the total metal (E+E') corresponds to the amount of anion required to balance the cation charge provided by the E, E' and Y components.

It will be evident that providing single phase precursors as described arranges the two components, E and E', in a structured arrangement where E and E' are closely connected through the Z, $H_2O$ and/or Y components. Various structures may be produced (e.g., orthorhombic or cubic). In any case, as a result of the arrangement of the components in the precursor, when the single phase structure collapses upon heating, uniformly interspersed phases of E and E' are formed. These are referred to herein as "homogeneously dispersed" phases.

It is desirable to convert the single phase precursor to multiphase composition at a moderately elevated temperature (e.g., about 600° C. or less). While some single phase structures are unstable and collapse upon heating, this conversion is ordinarily accomplished by decomposing the decomposable groups and/or removing water from the precursor. Accordingly, the decomposable oxygen-containing groups (when present) and the decomposable cations (when present) preferably decompose at about 600° C. or less. It is also desirable that water, when present, is substantially removed at about 600° C. or less.

The catalysts used for changing the fluorine content of halogenated hydrocarbons should contain fluoride (as a fluoride or in combination with other anions as in oxyfluorides). When the multiphase composition produced by heating the single phase precursor contains no fluoride, the chloride, bromide and/or oxide present may be at least partially converted to fluoride by contacting the multiphase composition with a vaporizable fluorine-containing fluorinating compound. Even when the multiphase composition produced by heating the single phase precursor does contain fluoride, together with other anions, a more active catalyst may often be achieved by contacting the multiphase composition with a vaporizable fluorine-containing fluorinating compound. Typically, where additional fluoride is desired, a multiphase composition is treated with a vaporizable fluorine-containing fluorinating compound such as HF, $SF_4$, $COF_2$, $CCl_3F$, $CCl_2F_2$, $CHF_3$ or $CCl_2FCClF_2$, at elevated temperatures (e.g., at about 200° C. to about 450° C.) until the desired degree of fluorination is obtained (see, e.g., U.S. Pat. No. 4,902,838).

Included in this invention is a process for increasing the fluorine content of a saturated or olefinic compound having the formula $C_nH_aF_bX_c$ where n is an integer from 1 to 6, a is an integer from 0 to 12, b is an integer from 0 to 13, c is an integer from 0 to 13, provided that c is at least 1 when the compound is saturated and each X is independently selected from Cl and Br, by reacting said compound with HF in the vapor phase; a process for decreasing the fluoride content of a saturated compound having the formula $C_mH_dF_eX_f$ where m is an integer from 1 to 6, d is an integer from 0 to 4, e is an integer from 1 to 13, f is an integer from 0 to 12, and each X is independently selected from Cl and Br, by reacting said compound with HCl in the vapor phase; and a process for the disproportionation of a compound having the formula $C_pH_gF_hCl$ where p is an integer from 1 to 2, g is an integer from 1 to 3, and h is an integer from 1 to 4. These processes are respectively characterized by reacting the $C_nH_aF_bX_c$ compound with HF, reacting the $C_mH_dF_eX_f$ compound with HCl, and conducting the disproportionation of the $C_pH_gF_hCl$ compound, in the presence of a multiphase catalyst containing fluorine which has a phase containing E homogeneously dispersed with a phase containing E' and/or is prepared by heating the above defined single phase catalyst precursor of the formula $E_uE'_{1-u}Z_v(H_2O)_wY_z$. Preferably, these processes are conducted in the presence of a multiphase catalyst composition consisting essentially of fluorides of at least one divalent element selected from the group consisting of Mn, Co, Zn, Mg, and Cd and at least one trivalent element selected from the group consisting of Al, Ga, Cr and V, provided that Cr is not more than about 10 atom percent of said trivalent elements, which have phases of said divalent fluorides homogeneously dispersed with phases of said trivalent fluorides and/or are prepared by heating a single phase fluoride compositions of the formula $MM'F_5(H_2O)_2$ or the formula $NH_4MM'F_6(H_2O)$ as defined herein.

Single-phase fluoride compositions of the formula $MM'F_5(H_2O)_2$ may be prepared by dissolving oxides or salts of M and M' (the relative amounts chosen so that the atomic ratio M:M' is essentially 1:1) in aqueous HF at room temperature and evaporating the solution to dryness (e.g., at a temperature of from about 100° C. to 130° C.). Preferably, the recovered solid is dried at about 110° C. for 12 hours. For example, quantities of reactants in the form of oxides, hydroxides, nitrates, fluorides and/or carbonates of M and M' which are chosen to provide the desired atomic ratio of M:M' can be individually dissolved in 48% aqueous HF and mixed (e.g., in a 500 ml Teflon® flask); the mixture can then be heated to about 100° C. to remove excess HF, (the HF vapors may be condensed and collected); and the residue can be recovered and dried at 110° C. in a vacuum drying oven for 12 hours. (Reference is also made to the technique for preparing iron-containing fluorohydrates containing divalent and trivalent cations as disclosed in P. Charpin et al., *C. R. Acad. Sci. Paris*, C280, 61–64 (1975), T. W. Balcerekm et al., *J. Inorg. & Nucl. Chem.*, 40. 773 (1978), and Y. Laligant, et al., *Chemica Scripta*, 28, 101 (1988).)

Alternatively, the single-phase fluoride compositions can be prepared by direct precipitation from aqueous chloride solutions of divalent M and trivalent M', using HF as a precipitant. The precipitate is filtered and washed with distilled water and dried at about 110° C. For example, quantities of the reactants in the form of chlorides of M and M' which are chosen to provide the desired atomic ratio of M:M' and are dissolved in distilled water and mixed in a container (e.g., in a Teflon® beaker); a ten-fold excess of 48% aqueous HF may be added to the above solution under stirring; and the precipitate formed may be recovered by filtration, washed with distilled water and dried at about 110° C. for about 12 hours.

The lattice parameters of these single-phase fluoride compositions are determined from x-ray diffraction powder patterns. The thermogravimetric analysis of these fluorides from room temperature to 600° C. shows weight loss corresponding to 2 moles of $H_2O$ per mole of $MM'F_5(H_2O)_2$.

Of note are embodiments where M is from 1 to 99 atom percent of one divalent metal (e.g., Zn or Co) with the remainder being one or more of the other divalent metals. Examples include embodiments where M comprises zinc and cobalt and where M comprises zinc and magnesium. Also of note are embodiments where M' is from 1 to 99 atom percent of one trivalent metal (e.g., Al or Ga) with the remaining being one or more of the other trivalent metals. Examples include embodiments where M' comprises aluminum and chromium.

The single-phase fluoride compositions of the formula $MM'F_5(H_2O)_2$ may be used to prepare multiphase compositions consisting essentially of fluorides of at least one divalent element selected from the group consisting of Mn, Co, Zn, Mg and Cd and at least one trivalent element selected from the group consisting of Al, Ga, Cr and V suitable for use as catalysts. This may be accomplished by heating these single-phase compositions at about 300° C. to 350° C. for a suitable period (e.g., typically 1 hour or more). The multiphase catalysts obtained by this method are characterized by having homogeneously dispersed fluorides of the divalent and trivalent elements. It will be understood that as $H_2O$ is removed from these single phase compositions, the crystal structure of the single phase composition collapses, resulting in the formation of multiple phases of metal fluorides.

Homogeneously dispersed multiphase compositions suitable for use as catalysts may also be prepared from single-phase fluoride compositions having the formula $NH_hdMM'F_6(H_2O)$. This may be accomplished by heating these single phase compositions at about 400° C. to 450° C. for a suitable period (typically 1 hour or more). The multiphase catalysts obtained by this method are similar to those obtained from $MM'F_5(H_2O)_2$ and are characterized by having homogeneously dispersed divalent metal fluoride and trivalent metal fluoride phases. Compositions of the formula $NH_4MM'F_6(H_2O)$ may be prepared by precipitation of the compositions from aqueous chloride solutions of the metals and ammonium using aqueous HF as the precipitant. It will be understood that as $H_2O$ and $NH_4F$ are removed from these single phase compositions, the crystal structure of the single phase composition collapses, resulting in the formation multiple phases of metal fluorides.

The catalyst preparation methods of this invention include a method of preparing a multiphase catalyst composition consisting essentially of fluorides of at least one divalent metal selected from the group consisting of Mn, Co, Zn, Mg and Cd and at least one trivalent metal selected from the group consisting of Al, Ga, Cr and V, wherein when Co is present another of said divalent metals is also present and Cr is not more than about 10 mole percent of said trivalent metals. These embodiments are characterized by heating a single phase fluoride composition of the formula $MM'F_5(H_2O)_2$ or the formula $NH_4MM'F_6(H_2O)$ when M is at least one divalent element selected from the group consisting of Mn, Co, Zn, Mg and Cd, provided that when Co is used another of said divalent elements is also used and M' is at least one trivalent element selected from the group consisting of Al, Ga, Cr and V, provided that Cr is not more than 10 atom percent of said trivalent elements at a temperature sufficient to substantially remove $H_2O$, and $NH_4F$ when $NH_4$ is present, bound in said single phase fluoride composition. The catalysts of this invention include multiphase catalyst compositions consisting essentially of fluorides of at least one divalent element and at least one trivalent element prepared in accordance with these embodiments; and these catalysts may be used for the process for increasing the fluorine content of compounds of the formula $C_nH_aF_bX_c$, the process for decreasing the fluorine content of compounds of the formula $C_mH_dF_eX_f$, and for the process for the disproportionation of compounds of the formula $C_pH_gF_hCl$, as described herein.

Of note are embodiments of multiphase catalyst compositions derived from $MAlF_5(H_2O)_2$ or $NH_4MAlF_6(H_2O)$ (i.e., the trivalent metal, M', is aluminum) where the trivalent fluoride is β-aluminum fluoride.

Homogeneously dispersed multiphase catalysts of fluorides of divalent and trivalent elements may be used in accordance with this invention in a process for increasing the fluorine content of compounds of the formula $C_nH_aF_bX_c$ having from 1 to 6 carbon atoms and when the compound is saturated at least one X (i.e., Cl or Br), by reacting said compounds with HF in the vapor phase in the presence of such catalysts. Of note are embodiments where X is Cl. Suitable catalysts for this reaction include compositions consisting essentially of fluorides of at least one divalent element selected from the group consisting of Mn, Co, Zn, Mg, and Cd homogeneously dispersed with fluorides of at least one trivalent element selected from the group consisting of Al, Ga, Cr and V, provided that Cr is not more than about 10 atom percent of said trivalent elements.

The reaction of said compounds of the formula $C_nH_aF_bX_c$ with HF in the presence of the catalysts of the instant invention is typically conducted at about 150° C. to 500° C., preferably for saturated compounds at about 175° C. to 400° C., and more preferably for saturated compounds at about 200° C. to about 350° C., with a contact time of about 1 to about 120 seconds, preferably about 5 to about 60 seconds. The amount of HF ordinarily should be at least a stoichiometric amount. Typically, the molar ratio of HF to the said compounds of the formula $C_nH_aF_bX_c$ can range from about 1:1 to about 100:1, preferably about 2:1 to 50:1, and more preferably about 3:1 to 10:1. In general, with a given catalyst composition, the higher the temperature and the longer the contact time, the greater is the conversion to fluorinated products. The above variables can be balanced, one against the other, so that the formation of higher fluorine substituted products is maximized.

Examples of olefinic compounds which may be reacted with HF include $CHCl=CCl_2$, $CCl_2=CCl_2$, $CCl_3CCl=CClCCl_3$, $CCl_2=CH_2$, $CHF=CF_2$, $CF_2=CH_2$ and $CF_2=CFCl$. Of note is a catalytic process for producing 2-chloro-1,1,1-trifluoroethene (HCFC-133a) by the fluorination of a trihaloethene of the formula $CX_2=CHCl$ wherein each X is chlorine or fluorine. Starting materials include trichloroethene, 1,2-dichlorofluoroethene and 1-chloro-2,2-difluoroethene. Trichloroethene is preferred. HCFC-133a is produced by reacting the above unsaturated compounds with HF in the vapor phase in the presence of the catalysts of this invention. The reaction of the above trihaloethenes with HF in the presence of the catalysts of the instant invention is preferably conducted at about 150° C. to 350° C., more preferably about 175° C. to 250° C. Oxygen may be added, if desired.

Also of note is a catalytic process for producing 2,2-dichloro-1,1,1-trifluoroethane ($CHCl_2CF_3$, i.e., HCFC-123), 1,1,1,2-tetrafluorochloroethane ($CHClFCF_3$, i.e., HCFC-124) and pentafluoroethane ($CHF_2CF_3$, i.e., HFC-125) by the fluorination of a tetrahaloethene of the formula $C_2Cl_{4-x}F_x$, wherein x equals 0 to 3. Starting materials include $CCl_2=CCl_2$, $CClF=CCl_2$, $CClF=CClF$ $CF_2=CCl_2$, and $CF_2=CClF$. Tetrachloroethene is preferred. HCFC-123, HCFC-124 and/or HFC-125 is produced by reacting the above unsaturated compounds with HF in the vapor phase In the presence of the catalysts of this invention.

Examples of saturated compounds which may be reacted with HF include $CH_2Cl_2$, $CHCl_3$, $C_2Cl_6$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, and $C_2HClF_4$. Of note are catalytic processes for reacting 1,1,1-trichloro-2,2,2-trifluoroethane (i.e., $CCl_3CF_3$, CFC-113a), or reacting dichloromethane, with HF, in the vapor phase in the presence of the catalysts of this invention. For the reaction of CFC-113a with HF to yield $CCl_2FCF_3$ (CFC-114a), the HF:$CCl_3CF_3$ ratio can vary widely. The HF:CFC-113a ratio should be at least stoichiometric but preferably can vary from about 2:1 to about 10:1.

For the reaction of dichloromethane to yield difluoromethane ($CH_2F_2$, HFC-32), the molar ratio of HF to $CH_2Cl_2$ preferred ranges from about 1:1 to about 10:1. The reaction temperature normally ranges from about 180° C. to about 375° C. (e.g., from about 200° C. to about 350° C.).

Homogeneously dispersed multiphase catalysts of fluorides of divalent and trivalent elements may be used in accordance with this invention in a process for decreasing the fluorine content of a saturated compound having the formula $C_mH_dF_eX_f$ having from 1 to 6 carbon atoms and at least one fluorine, by reacting such compounds with HCl in the vapor phase in the presence of such catalysts. Suitable catalysts for this reaction include compositions consisting essentially of fluorides of at least one divalent element selected from the group consisting of Mn, Co, Zn, Mg, and Cd homogeneously dispersed with fluorides of at least one trivalent element selected from the group consisting of Al, Ga, Cr, and V, provided that Cr is not more than about 10 atom percent of said trivalent elements.

The reaction of said compounds of the formula $C_mH_dF_eX_f$ with HCl in the presence of the catalysts of the instant invention is typically conducted at about 225° C. to 450° C., preferably from about 250° C. to about 350° C. The amount of HCl should be at least a stoichiometric amount. Generally, the molar ratio of HCl to the $C_mH_dF_eX_f$ compound ranges from about 2:1 to about 100:1, preferably about 3:1 to 50:1, and more preferably about 5:1 to 20:1.

Chlorine may be present in some process embodiments, either as an initial reactant or as an in-situ formed product.

Oxygen may be added if desired. The amount of oxygen present during the contacting step relative to the molar concentration of the $C_mH_dF_eX_f$ can also vary but will generally range from 0.001 to 1.0 moles. The oxygen may be fed to the reactor as such or may be diluted with an inert gas such as nitrogen, helium or argon. The source of the oxygen may also be air containing molecular oxygen.

In general, with a given catalyst composition, the higher the temperature and the longer the contact time, the greater is the conversion of the $C_mH_dF_eX_f$ compound to chlorinated products. The above variables can be balanced, one against the other, so that the reaction is optimized.

Examples of saturated compounds that can be reacted with HCl include $C_2Cl_4F_2$, $C_2Cl_3F_3$, $C_2Cl_2F_4$, $C_2ClF_5$, $CH_2FCF_3$, $CHF_3$, $CHF_2CF_3$, $CH_3CF_3$, $CH_3CHF_2$, $CHCl_2F$, $CHClF_2$, $CHCl_2CF_3$, $CHClFCF_3$, $CH_2ClCF_3$, $CH_3ClF_2$, $CHBrF_2$ and $CHBrCF_3$. Of note is a process for selectively reacting 1,1-dichloro-1,2,2,2-tetrafluoroethane ($CCl_2FCF_3$) with HCl in the presence of its isomer, 1,2-dichloro-1,1,2, 2-tetrafluoroethane ($CClF_2CClF_2$) in the vapor phase in the presence of the catalyst of this invention. The process is especially useful for enriching $CClF_2CClF_2$ from initial mixtures wherein the $CCl_2FCF_3$ content is equal to or greater than the $CClF_2CClF_2$ content. Preferably, the fraction of total $C_2Cl_2F_4$ which is $CCl_2FCF_3$ is reduced by at least 25%. The initial mixture may consist essentially of $C_2Cl_2F_4$ isomers, or may contain other compounds which do not interfere with the selective reaction of $CCl_2FCF_3$. Typically, the reaction is controlled to provide $CCl_3CF_3$ as the major chlorination product of $CCl_2FCF_3$. The reaction of mixtures of $CClF_2CClF_2$ and $CCl_2FCF_3$ with HCl in the presence of the catalysts of the instant invention is preferably conducted at about 250° C. to 350° C., with a contact time of about 1 to about 120 seconds, preferably about 5 to about 60 seconds.

The reaction products are separated by conventional techniques, such as distillation. Some of the reaction products will have desired properties for commercial use. For example $CCl_3CF_3$ (CFC-113a) can be used to prepare CFC-114a which can then be converted to $CH_2FCF_3$ (HFC-134a) by hydrodechlorination. Others, such as $CCl_2=CCl_2$ can be recycled back to reactors which are being used for the synthesis of halofluorocarbons.

Homogeneously dispersed multiphase catalysts of fluorides of divalent and trivalent elements may be used in accordance with this invention in a catalytic process for the disproportionation of hydrochlorofluorocarbons of the formula, $C_pH_gF_hCl$ having from 1 to 2 carbon atoms, at least one hydrogen and at least one fluorine, to produce hydrofluorocarbons. Suitable catalysts for this reaction include compositions consisting essentially of fluorides of at least one divalent element selected from the group consisting of Mn, Co, Zn, Mg, and Cd homogeneously dispersed with fluorides of at least one trivalent element selected from the group consisting of Al, Ga, Cr, and V, provided that Cr is not more than about 10 atom percent of said trivalent elements.

Suitable hydrochlorofluorocarbons for disproportionation include $CH_2ClF$, $CH_3CClF_2$, and $CHClFCF_3$. The products of the disproportionation reactions are respectively, $CH_2F_2$ and $CH_2Cl_2$, $CH_3CF_3$ and $CH_2=CCl_2$, and $CHCl_2CF_3$ and $CHF_2CF_3$.

Reactions for changing the fluorine content of a halogenated hydrocarbon (e.g., the reaction of the compounds of the formula $C_nH_aF_bX_c$ with HF, the reaction of the compounds of the formula $C_mH_dF_eX_f$ with HCl and the disproportionation of the compounds of the formula $C_pH_gF_hCl$) may be conducted in any suitable reactor, including fixed and fluidized bed reactors. The reaction vessel should be constructed from materials which are resistant to the corrosive effects of hydrogen fluoride and hydrogen chloride such as Inconel™ nickel alloy and Hastelloy™ nickel alloy.

Pressure is not critical for these reactions. Atmospheric and superatmospheric pressures are the most convenient and are therefore preferred.

The reaction products may be separated by conventional techniques such as distillation. It is noted that many halogenated hydrocarbon products of the above reactions form azeotropes with HF, HCl, or other halogenated hydrocarbons.

The homogeneously dispersed multiphase compositions obtained herein from single phase $MM'F_5(H_2O)_2$ or $NH_4MM'F_6(H_2O)$ are also useful for preparing initiators for telomerization of polyfluoroalkyliodides with polyfluoroolefins. For example, granulated compositions containing $AlF_3$ together with either $MnF_2$ or $CoF_2$ can respectively be fluorinated with elemental fluorine to compositions containing $AlF_3$ together with either $MnF_3$ or $CoF_3$, and these resulting compositions can be used as initiators for the reaction of tetrafluoroethylene with $C_5F_{13}I$ or $C_2F_5I$ to produce telomeric perfluoroalkyliodides. Reference is made to U.S. patent application Ser. No. 08/249,311 for further discussion of such telomerizations.

Practice of the invention will become further apparent from the following non-limiting Examples.

EXAMPLES 1–10

Examples 1–10 were carried out using essentially the same procedure.

To make a composition having the formula $MM'F_5(H_2O)_2$, quantities of hydroxides, oxides, fluorides, and/or carbonates of M and M' corresponding to a M:M' ratio of 1:1 were dissolved separately in 48% aqueous HF and mixed together in a Teflon® container and the solution was evaporated to dryness. The specific quantities used in each Examples are shown in Table I. In each instance the residue or solid was recovered, ground to a powder, and dried at about 110° C. for about 12 hours.

The x-ray diffraction pattern of each of the products showed that the product was essentially a single phase. The orthorhombic lattice parameters of the products were determined from the x-ray diffraction powder patterns and are shown in Table II.

The compositions of Examples 1–5 were heated to from 300° C. to 350° C. for from 3 to 12 hours and the X-ray diffraction patterns of the resulting products showed the presence of $MF_2$ (M=Zn, Co, Mn, Mg or Cd) and $\beta$-$AlF_3$.

EXAMPLES 11–15

$[Zn_xCo_yAlF_5(H_2O)_2]$

To make a composition of having the formula $Zn_xCo_yAlF_5(H_2O)_2$ where x is from 0.02 to 0.90 and y is from 0.10 to 0.98 (and x+y=1.00) quantities of oxides or hydroxides of Zn, Co or Al taken in the ratio Zn:Co:Al= x:y:1.0 were dissolved in 48% aqueous HF and mixed together in a Teflon® container and the solution was evaporated to dryness. The specific quantities used are shown in Table I. In each instance the residue or solid was recovered, ground to a powder, and dried at 110° C. for about 12 hours.

The x-ray diffraction pattern of each of the products showed that the product was essentially a single phase. The orthorhombic lattice parameters of the products were determined from the x-ray diffraction powder patterns and are shown in Table II.

The compositions were heated to 300° C. to 350° C. for 3 to 12 hours and the X-ray diffraction patterns of the resulting products showed the presence of $MF_2$ (M=Zn, Co) and $\beta$-$AlF_3$.

TABLE I

| EXAMPLE | COMPOSITION | TRIVALENT METAL REACTANT | DIVALENT METAL REACTANT |
|---|---|---|---|
| 1 | $ZnAlF_5(H_2O)_2$ | 12.480 g $Al(OH)_3$[a] | 13.0192 g $ZnO$[d] |
| 2 | $CoAlF_5(H_2O)_2$ | 2.3400 g $Al(OH)_3$[a] | 2.7885 g $Co(OH)_2$[e] |
| 3 | $MnAlF_5(H_2O)_2$ | 2.3400 g $Al(OH)_3$[a] | 3.4485 g $MnCO_3$[f] |
| 4 | $MgAlF_5(H_2O)_2$ | 0.7800 g $Al(OH)_3$[a] | 0.5832 g $Mg(OH)_2$[g] |
| 5 | $CdAlF_5(H_2O)_2$ | 0.7800 g $Al(OH)_3$[a] | 1.5044 g $CdF_2$[h] |
| 6 | $ZnGaF_5(H_2O)_2$ | 0.9372 g $Ga_2O_3$[b] | 0.8137 g $ZnO$[d] |
| 7 | $MnGaF_5(H_2O)_2$ | 0.9372 g $Ga_2O_3$[b] | 1.1495 g $MnCO_3$[f] |
| 8 | $CdGaF_5(H_2O)_2$ | 0.0372 g $Ga_2O_3$[b] | 1.5044 g $CdF_2$[h] |
| 9 | $ZnVF_5(H_2O)_2$ | 0.7494 g $V_2O_3$[c] | 0.8137 g $ZnO$[d] |
| 10 | $MnVF_5(H_2O)_2$ | 0.7494 g $V_2O_3$[c] | 1.1495 g $MnCO_3$[f] |
| 11 | $Zn_{0.1}Co_{0.9}AlF_5(H_2O)_2$ | 7.8000 g $Al(OH)_3$[a] | 0.8137 g $ZnO$[d] + 8.3600 g $Co(OH)_2$[e] |
| 12 | $Zn_{0.9}Co_{0.1}AlF_5(H_2O)_2$ | 7.8000 g $Al(OH)_3$[a] | 7.3233 g $ZnO$[d] + 0.9295 g $Co(OH)_2$[e] |
| 13 | $Zn_{0.02}Co_{0.98}AlF_5(H_2O)_2$ | 7.800 g $Al(OH)_3$[a] | 0.1627 g $ZnO$(d) + 9.1091 g $Co(OH)_2$[e] |
| 14 | $Zn_{0.04}Co_{0.96}AlF_5(H_2O)_2$ | 7.800 g $Al(OH)_3$[a] | 0.4882 g $ZnO$[d] + 8.9232 g $Co(OH)_2$[e] |
| 15 | $Zn_{0.06}Co_{0.94}AlF_5(H_2O)_2$ | 7.800 g $Al(OH)_3$[a] | 0.4882 g $ZnO$[d] + 8.7373 g $Co(OH)_2$[e] |

[a]Tech. grade $Al(OH)_3$ from Alfa Inorganics
[b]>99.9% $Ga_2O_3$ from Johnson & Matthey Company
[c]>99.9% $V_2O_3$ from Johnson & Matthey Company
[d]General reagent $ZnO$ from E. Merck
[e]99% $Co(OH)_2$ from Aldrich Chemical Company
[f]Tech. grade $MnCO_3$ from Alfa Inorganics
[g]>95% $Mg(OH)_2$ from Aldrich Chemical Company
[h]99.99% $CdF_2$ from Aldrich Chemical Company

TABLE II

| | Lattice Parameters of $M^{2+}M'^{3+}F_5(H_2O)_2$ Compositions | | | |
|---|---|---|---|---|
| EXAMPLE | COMPOSITION | a (nm) (±0.0002) | b (nm) (±0.0004) | c (nm) (±0.0002) |
| 1 | $ZnAlF_5(H_2O)_2$ | 0.7141 | 1.0307 | 0.6645 |
| 2 | $CoAlF_5(H_2O)_2$ | 0.7193 | 1.0353 | 0.6608 |
| 3 | $MnAlF_5(H_2O)_2$ | 0.7229 | 1.0487 | 0.6816 |
| 4 | $MgAlF_5(H_2O)_2$ | 0.7057 | 1.0126 | 0.6796 |
| 5 | $CdAlF_5(H_2O)_2$ | 0.7331 | 1.0639 | 0.6829 |
| 6 | $ZnGaF_5(H_2O)_2$ | 0.7380 | 1.0600 | 0.6584 |
| 7 | $MnGaF_5(H_2O)_2$ | 0.7471 | 1.0735 | 0.6720 |
| 8 | $CdGaF_5(H_2O)_2$ | 0.7603 | 1.0875 | 0.6718 |
| 9 | $ZnVF_5(H_2O)_2$ | 0.7486 | 1.0756 | 0.6589 |
| 10 | $MnVF_5(H_2O)_2$ | 0.7607 | 1.0912 | 0.6728 |
| 11 | $Zn_{0.1}Co_{0.9}AlF_5(H_2O)_2$ | 0.7174 | 1.0314 | 0.6646 |

TABLE II-continued

Lattice Parameters of $M^{2+}M'^{3+}F_5(H_2O)_2$ Compositions

| EXAMPLE | COMPOSITION | a (nm) (±0.0002) | b (nm) (±0.0004) | c (nm) (±0.0002) |
|---|---|---|---|---|
| 12 | $Zn_{0.9}Co_{0.1}AlF_5(H_2O)_2$ | 0.7146 | 1.0310 | 0.6645 |
| 13 | $Zn_{0.02}Co_{0.98}AlF_5(H_2O)_2$ | 0.7152 | 1.0299 | 0.6589 |
| 14 | $Zn_{0.04}Co_{0.96}AlF_5(H_2O)_2$ | 0.7157 | 1.0306 | 0.6590 |
| 15 | $Zn_{0.06}Co_{0.94}AlF_5(H_2O)_2$ | 0.7172 | 1.0322 | 0.6167 | a, b, c are lattice parameters of an orthorhombic unit cell

EXAMPLE 16

[$NH_4MgAlF_6 \cdot H_2O$]

To make a composition having the formula $NH_4MgAlF_6 \cdot H_2O$ quantities of $NH_4Cl$ (0.5349 g), $MgCl_2 \cdot 6H_2O$ (2.0330 g) and $AlCl_3 \cdot 6H_2O$ (2.3980 g) corresponding to a mole ratio of 1:1:1 were dissolved in distilled water in a Teflon® beaker. To the solution was added 48% aqueous HF until the precipitation was complete. The white solid formed was filtered and washed with deionized water and dried at 110° C. for 12 hours.

The x-ray diffraction pattern of the product showed that the product was essentially single phase. The cubic lattice parameter of the product were determined from the x-ray diffraction powder pattern (a=0.99608 nm).

The composition was heated to 450° C. for 3 to 12 hours and the X-ray of the resulting product showed the presence of $MgF_2$ and $\beta$-$AlF_3$.

GENERAL PROCEDURE FOR EXAMPLES 17–32

A reactor, 11" (27.9 cm)×½" (1.3 cm) Inconel™ nickel alloy tube containing an internal thermowell, containing 12 to 15 mL of catalyst (10 to 14 mesh, i.e., 1.7 to 1.3 mm), was heated in a fluidized sandbath. The feed to the reactor was measured through mass flow controllers, or when liquids were used, they were metered by liquid metering pumps. The liquid feeds were vaporized and mixed with HF or nitrogen as appropriate, prior to entering the reactor. All experiments were performed at ambient pressure. The products from the reactor were analysed by on line GC/MS. The results are shown in the tables included with the examples. In the tables HRS. is hours and R.T. is the reaction temperature. The $CH_2Cl_2$ feeds contained about 99% $CH_2Cl_2$, and about 1% F31. The molar ratio of HF:$CH_2Cl_2$ was about 4:1 and the contact time was about 15 seconds in all cases. The F113a feeds contained about 98.6% F113a and about 1.4% F114a. The molar ratio of HF:F113a was about 2:1 and the contact time was about 30 seconds in all cases.

EXAMPLE 17

FLUORINATION OF ETHYLENE CHLORIDE $MnF_2/\beta$-$AlF_3$ (Product of Example 3; 12.5 g, 12 mL)

$CH_2Cl_2 + HF \rightarrow CH_2ClF + CH_2F_2$

| | | Mole % | | |
|---|---|---|---|---|
| HRS. | R.T. (°C.) | F32 | F31 | $CH_2Cl_2$ |
| 2.5 | 250 | 1.3 | 8.2 | 90.6 |
| 3.5 | 275 | 1.4 | 8.6 | 90.1 |

F32 is $CH_2F_2$
F31 is $CH_2ClF$

EXAMPLE 18

FLUORINATION OF F113a $MnF_2/\beta$-$AlF_3$ (Product of Example 3; 12.5 g, 12 mL)

$CCl_3CF_3 + HF \rightarrow CCl_2FCF_3$

| | | Mole % | |
|---|---|---|---|
| HRS. | R.T. (°C.) | F114a | 113a |
| 0.5 | 275 | 2.4 | 97.5 |
| 2.0 | 300 | 2.5 | 97.4 |
| 2.5 | 325 | 2.5 | 97.4 |
| 3.0 | 350 | 2.9 | 97.0 |

F114a is $CCl_2FCF_3$
F113a is $CCl_3CF_3$

EXAMPLE 19

FLUORINATION OF F113a $ZnF_2/\beta$-$AlF_3$ (Product of Example 1; 16.1 g, 15 mL)

| | | Mole % | | |
|---|---|---|---|---|
| HRS. | R.T. (°C.) | F114a | F113 | 113a |
| 1.0 | 200 | 2.4 | 0.1 | 97.4 |
| 2.0 | 250 | 3.3 | 0.1 | 96.6 |
| 3.0 | 300 | 6.4 | 0.1 | 93.5 |
| 4.0 | 350 | 11.5 | 0.0 | 88.4 |
| 5.0 | 350 | 9.9 | 0.0 | 90.0 |

F113 is $CCl_2FCClF_2$

EXAMPLE 20

FLUORINATION OF METHYLENE CHLORIDE $ZnF_2/\beta$-$AlF_3$ (Product of Example 1; 16.1 g, 15 mL)

| HRS. | R.T. (°C.) | Mole % | | |
|---|---|---|---|---|
| | | F32 | F31 | $CH_2Cl_2$ |
| 1.5 | 300 | 16.5 | 16.1 | 67.4 |

EXAMPLE 21

FLUORINATION OF METHYLENE CHLORIDE $ZnF_2/CoF_2/\beta$-$AlF_3$ (Product of Example 11; 15.0 g, 15 mL)

| HRS. | R.T. (°C.) | Mole % | | |
|---|---|---|---|---|
| | | F32 | F31 | $CH_2Cl_2$ |
| 5.5 | 250 | 51.9 | 12.5 | 35.6 |
| 7.0 | 275 | 46.6 | 13.9 | 39.5 |

EXAMPLE 22

FLUORINATION OF F113a $ZnF_2/CoF_2/\beta$-$AlF_3$ (Product of Example 11; 15.0 g, 15 mL)

| HRS. | R.T. (°C.) | Mole % | |
|---|---|---|---|
| | | F114a | 113a |
| 1.5 | 200 | 3.2 | 96.6 |
| 2.0 | 225 | 4.6 | 95.1 |
| 2.5 | 250 | 6.2 | 93.4 |
| 3.0 | 275 | 8.8 | 91.0 |
| 3.5 | 300 | 13.9 | 79.6 |
| 5.5 | 350 | 23.2 | 76.4 |

EXAMPLE 23

FLUORINATION OF F113a $CoF_2/\beta$-$AlF_3$ (15.0 g, 15 mL)

The catalyst used in this example was prepared in a manner similar to the procedure in A. Demsar et al., Thermochemica Acta (92), 665–668 (1985). $(NH_3)_6CoCl_3$ of >95% purity (3740 g) and $AlCl_3.6H_2O$ (12.0715 g), in a 1:1 mole ratio, were weighed into separate Teflon® beakers and dissolved in distilled water (50 mL). 48% HF (100 mL) was added to the cobalt chloride containing solution. The $AlCl_3$ solution was added to the cobalt chloride solution with stirring. The yellow precipitate obtained was filtered and dried at 110° C. for about 12 hours. The X-ray diffraction pattern showed the formation of a single phase material with a cubic lattice parameter of 0.986 nm. The structural formula of the single phase is $(NH_3)_6CoAlF_6$.

The above single phase composition was heated to 350° C. for about 12 hours and the X-ray diffraction pattern of the product showed the presence of $CoF_2/\beta$-$AlF_3$. The product was granulated to form 1.3 to 1.7 mm size particles, and used for fluorination of F113a, with the following results.

| HRS. | R.T. (°C.) | Mole % | |
|---|---|---|---|
| | | F114a | 113a |
| 1.0 | 200 | 1.5 | 98.4 |
| 2.0 | 250 | 1.6 | 98.4 |
| 3.5 | 300 | 1.6 | 98.3 |
| 4.5 | 350 | 1.9 | 97.9 |

EXAMPLE 24

FLUORINATION OF METHYLENE CHLORIDE $CoF_2/\beta$-$AlF_3$ (15.0 g, 15 mL)

The catalyst used was prepared in the same manner as that used in Example 23.

| HRS. | R.T. (°C.) | Mole % | | |
|---|---|---|---|---|
| | | F32 | F31 | $CH_2Cl_2$ |
| 1.0 | 300 | 3.5 | 8.5 | 88.0 |

EXAMPLE 25

FLUORINATION OF F113a $ZnF_2/CoF_2/\beta$-$AlF_3$ (Product of Example 13, 13.7 g, 15 mL)

| HRS. | R.T. (°C.) | Mole % | |
|---|---|---|---|
| | | F114a | 113a |
| 1.0 | 250 | 13.9 | 86.1 |
| 2.0 | 275 | 19.9 | 80.0 |
| 2.5 | 300 | 28.7 | 71.1 |
| 3.0 | 325 | 31.8 | 68.1 |
| 4.0 | 350 | 38.0 | 61.9 |

EXAMPLE 26

FLUORINATION OF METHYLENE CHLORIDE $ZnF_2/CoF_2/\beta$-$AlF_3$ (Product of Example 13, 13.7 g, 15 mL)

| HRS. | R.T. (°C.) | Mole % | | |
|---|---|---|---|---|
| | | F32 | F31 | $CH_2Cl_2$ |
| 0.5 | 175 | 29.7 | 12.8 | 57.5 |
| 1.5 | 200 | 42.9 | 11.1 | 45.9 |
| 2.5 | 225 | 51.2 | 11.9 | 37.1 |
| 3.0 | 250 | 54.8 | 12.4 | 32.7 |

EXAMPLE 27

FLUORINATION OF F113a $ZnF_2/CoF_2/\beta$-$AlF_3$ (Product of Example 12, 15.0 g, 15 mL)

| HRS. | R.T. (°C.) | Mole % | |
|---|---|---|---|
| | | F114a | 113a |
| 1.0 | 250 | 4.3 | 95.6 |
| 2.0 | 275 | 5.3 | 94.6 |
| 2.5 | 300 | 7.0 | 92.9 |
| 3.0 | 325 | 8.9 | 91.0 |
| 4.0 | 350 | 11.6 | 88.3 |

EXAMPLE 28

FLUORINATION OF METHYLENE CHLORIDE $ZnF_2/CoF_2/\beta$-$AlF_3$ (Product of Example 12, 15.0 g, 15 mL)

| HRS. | R.T. (°C.) | Mole % | | |
|---|---|---|---|---|
| | | F32 | F31 | $CH_2Cl_2$ |
| 2.0 | 250 | 10.5 | 13.9 | 75.6 |
| 3.0 | 275 | 17.2 | 15.6 | 67.1 |

Fluorination of Methylene Chloride

Catalyst Comparisons

| Ex. | R.T. (°C.) | Mole % | | |
|---|---|---|---|---|
| | | F32 | F31 | $CH_2Cl_2$ |
| 20 | 300 | 16.5 | 16.1 | 67.4 |
| 24 | 300 | 3.7 | 8.7 | 87.6 |
| 21 | 250 | 52.0 | 12.6 | 35.4 |

-continued

| Ex. | R.T. (°C.) | Mole % | | |
|---|---|---|---|---|
| | | F32 | F31 | $CH_2Cl_2$ |
| 17 | 250 | 1.2 | 8.1 | 90.5 |
| 26 | 250 | 54.8 | 12.4 | 32.7 |
| 28 | 250 | 10.5 | 13.9 | 75.6 |

Fluorination of 113a

Catalyst Comparisons at 350° C.

| Ex. | Mole % | |
|---|---|---|
| | F114a | 113a |
| 19 | 9.9 | 90.0 |
| 23 | 1.9 | 97.9 |
| 22 | 23.2 | 76.4 |
| 18 | 2.9 | 97.0 |
| 25 | 38.0 | 61.9 |
| 27 | 11.6 | 88.3 |

EXAMPLE 29

FLUORINATION OF TCE $ZnF_2/CoF_2/\beta$-$AlF_3$ (Product of Example 11; 15.0 g, 15 mL)

| HRS. | R.T. (°C.) | Mole % | | | | | | |
|---|---|---|---|---|---|---|---|---|
| | | F23 | F133a | F1121 | F132b | F1121 | F131a | TCE |
| 1.5 | 150 | 0.0 | 2.1 | 1.0 | 8.7 | 2.0 | 0.5 | 85.6 |
| 2.5 | 175 | 0.0 | 5.2 | 1.8 | 12.7 | 2.6 | 0.5 | 77.5 |
| 3.5 | 200 | 0.0 | 8.8 | 1.8 | 10.4 | 2.6 | 0.4 | 75.8 |
| 4.0 | 225 | 0.1 | 9.6 | 1.8 | 6.4 | 2.7 | 0.4 | 78.9 |
| 5.0 | 250 | 0.1 | 7.6 | 1.9 | 3.3 | 3.0 | 0.3 | 83.5 |

F23 is $CHF_3$
F133a is $CH_2ClCF_3$
F1121 is $CFCl=CHCl$ (both isomers)
F132b is $CH_2ClCClF_2$
F131a is $CH_2ClCCl_2F$
TCE is $CHCl=CCl_2$

EXAMPLE 30

Disproportionation of F142b over
$MgF_2/\beta$-$AlF_3$ $CH_3CClF_2 \rightarrow CH_3CF_3 + CH_2=CCl_2$ A vaporized sample of F142b mixed with nitrogen in a 1:2 molar ratio was passed over the $MgF_2/\beta$-$AlF_3$ catalyst (15 mL), prepared as described in Example 3, at various temperatures. The contact time was 30 seconds for all runs. Product analysis by on line chromatography and mass spectrometry showed the following.

| R.T. (°C.) | Mole % | | |
|---|---|---|---|
| | F143a | F142b | F1130a |
| 100 | 21.7 | 68.5 | 9.0 |
| 125 | 43.5 | 38.4 | 17.6 |
| 150 | 63.4 | 11.0 | 25.3 |
| 200 | 70.8 | 0.7 | 28.2 |
| 225 | 70.7 | 0.6 | 28.2 |
| 250 | 70.3 | 0.6 | 28.1 |

Small quantities of other products were present
F143a is $CH_3CF_3$
F142b is $CH_3CClF_2$
F1130a is $CH_2=CCl_2$

EXAMPLE 31

Disproportionation of F31 over $MgF_2/\beta$-$AlF_3$

A vaporized sample of F31 mxied with nitrogen in a 1:2 molar ratio was passed over the $MgF_2/\beta AlF_3$ catalyst (15 mL), prepared as described in Example 3, at various temperatures. The contact time was 30 seconds for all runs. Product analysis showed the following.

| R.T. (°C.) | Mole % | | |
|---|---|---|---|
| | F32 | F31 | $CH_2Cl_2$ |
| 150 | 22.9 | 46.5 | 30.6 |
| 175 | 37.7 | 11.6 | 50.6 |
| 200 | 37.9 | 11.1 | 51.0 |
| 250 | 36.9 | 13.1 | 49.9 |
| 300 | 36.7 | 15.2 | 48.0 |
| 350 | 35.2 | 17.0 | 47.7 |

EXAMPLE 32

Reaction of F114/F114a Mix and HCl over $MgF_2/\beta$-$AlF_3$

A 10:1 molar ratio of HCl and a commercial F114 mix containing 89.1% F114 and 10.8% F114a were passed over the $MgF_2/\beta$-$AlF_3$ catalyst (15 mL), prepared as described in Example 3, at various temperatures. Product analysis showed the following.

| R.T. (°C.) | Mole % | | | | |
|---|---|---|---|---|---|
| | F114 | F114a | F113 | 113a | PCE |
| 350 | 87.4 | 6.6 | 0.4 | 4.7 | 0.2 |
| 375 | 85.5 | 4.4 | 0.6 | 7.1 | 1.2 |
| 400 | 83.8 | 2.9 | 0.6 | 8.5 | 2.5 |

F114 is $CClF_2CClF_2$
PCE is $CCl_2=CCl_2$

Thus using the above catalyst the F114a is selectively degraded to provide a product enriched in F114. Small quantities of other products were present.

What is claimed is:

1. A single phase fluoride composition having the formula MM'F$_5$(H$_2$O)$_2$ wherein M is at least one divalent element selected from the group consisting of Mn, Co, Zn and Cd and M' is at least one trivalent element selected from the group consisting of Al, Ga and Cr, provided that Cr is not more than about 10 atom percent of M'.

2. A method of preparing a multiphase catalyst composition consisting essentially of fluorides of at least one divalent metal selected from the group consisting of Mn, Co, Zn, Mg and Cd and at least one trivalent metal selected from the group consisting of Al, Ga, Cr and V, wherein when Co is present another of said divalent metals is also present and Cr is not more than about 10 atom percent of said trivalent metals characterized by: heating a single phase fluoride composition of the formula MM'F$_5$(H$_2$O)$_2$ or the formula NH$_4$MM'F$_6$(H$_2$O) where M is at least one divalent element selected from the group consisting of Mn, Co, Zn, Mg and Cd, provided that when Co is used another of said divalent elements is also used and M' is at least one trivalent element selected from the group consisting of Al, Ga, Cr and V, provided that Cr is not more than about 10 atom percent of said trivalent elements to a temperature sufficient to substantially remove H$_2$O, and NH$_4$F when NH$_4^+$ is present, in said single phase fluoride composition.

3. A multiphase catalyst composition consisting essentially of fluorides of at least one divalent element and at least one trivalent element prepared in accordance with the process of claim 2.

4. The multiphase catalyst composition of claim 3 wherein M comprises zinc and cobalt.

5. The multiphase catalyst composition of claim 3 wherein M comprises zinc and magnesium.

6. The multiphase composition of claim 3 wherein M' comprises aluminum and chromium.

7. The multiphase catalyst composition of claim 3 wherein M is from 1 to 99 atom percent Zn.

8. The multiphase catalyst composition of claim 3 wherein M is from 1 to 99 atom percent Co.

9. The multiphase catalyst composition of claim 3 wherein M' is from 1 to 99 atom percent Al.

10. The multiphase catalyst composition of claim 3 wherein M' is from 1 to 99 atom percent Ga.

11. The multiphase catalyst composition of claim 3 wherein the preparation comprises treatment with a vaporizable fluorine-containing fluorinating compound at elevated temperatures.

12. The multiphase catalyst composition of claim 3 comprising $\beta$-aluminum fluoride.

13. The multiphase catalyst composition of claim 12 wherein the preparation comprises treatment with a vaporizable fluorine-containing fluorinating compound at elevated temperatures.

14. A multiphase catalyst composition consisting essentially of fluorides of at least one divalent element selected from the group consisting of Mn, Co, Zn, Mg and Cd, provided that when Co is used another of said divalent element is also used, and at least one trivalent element selected from the group consisting of Al, Ga, Cr and V, provided that Cr is not more than about 10 atom percent of said trivalent elements, wherein phases of said divalent fluorides are homogeneously dispersed with phases of said trivalent fluorides.

15. The multiphase catalyst composition of claim 14 comprising $\beta$-aluminum fluoride.

16. A single phase orthorhombic crystalline fluoride composition having the formula MM'F$_5$(H$_2$O)$_2$ wherein M is at least one divalent element selected from the group consisting of Mn, Co, Zn, Mg and Cd and M' is at least one trivalent element selected from the group consisting of Al, Ga and Cr, provided that Cr is not more than about 10 atom percent of M'.

* * * * *